US005734048A

United States Patent [19]

Kim et al.

[11] Patent Number: 5,734,048
[45] Date of Patent: Mar. 31, 1998

[54] PROCESS FOR MANUFACTURING CLAVULANIC ACID SALT

[75] Inventors: Jung Woo Kim; Nam Hee Choi, both of Seoul; Gang Sun Choi, Kyeonggi-Do; Don Wha Lee, Incheon, all of Rep. of Korea

[73] Assignee: Chong Kun Dang Corp., Seoul, Rep. of Korea

[21] Appl. No.: 554,699

[22] Filed: Nov. 7, 1995

[30] Foreign Application Priority Data

May 16, 1995 [KR] Rep. of Korea ............... 1995-12068

[51] Int. Cl.$^6$ .............................. C07D 503/18; A61K 31/42
[52] U.S. Cl. .............................................................. 540/349
[58] Field of Search ............................................. 540/349

[56] References Cited

U.S. PATENT DOCUMENTS

| | | | |
|---|---|---|---|
| 4,110,165 | 8/1978 | Cole et al. | 540/349 |
| 5,498,788 | 3/1996 | Zmitek | 540/349 |

FOREIGN PATENT DOCUMENTS

| | | |
|---|---|---|
| 827926 | 10/1975 | Belgium . |
| 0 026 044 | 8/1980 | European Pat. Off. . |
| 1 508 977 | 4/1974 | United Kingdom . |
| 1 543 563 | 2/1975 | United Kingdom . |
| 2 264 944 | 9/1993 | United Kingdom . |

*Primary Examiner*—Mark L. Berch
*Attorney, Agent, or Firm*—Nath & Associates; Gary M. Nath, Esq.; Karen Orzechowski

[57] ABSTRACT

According to the present invention, a process for manufacturing alkali metal salt of clavulanic acid wherein impure clavulanic acid in aqueous solution is extracted by a solvent mixture of ketone and alkyl acetate under acidic condition, treated in a conventional manner, and a solution of alkali metal salt of alkanoic acid dissolved in ketone or alkanol solvent is added to obtain pure alkali metal salt of clavulanic acid is provided.

Since the process according to the present invention omits a step of formation of amine salt, an economic and simple method for manufacturing alkali metal salt of clavulanic acid in a high yield without excessive use of solvent is provided.

7 Claims, No Drawings

PROCESS FOR MANUFACTURING CLAVULANIC ACID SALT

TECHNICAL FIELD

The present invention relates to a novel process for manufacturing salts of clavulanic acid represented by the following formula(I).

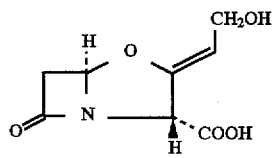

BACKGROUND ART

The resistance of β-lactam antibiotics is associated with inactivation of β-lactam structure due to the opening of β-lactam ring by β-lactamase produced by bacteria. Though the inactivating enzymes are commonly called as β-lactamase, they are largely divided into penicillinase and cephalosporinase, and their characteristics are different from one another dependent upon the species of microorganisms.

Clavulanic acid, an inhibitor of the β-lactamases, is produced from the culture solution of *Streptomyces clavuligerus*. Clavulanic acid itself has only weak antibacterial activity, but it potently enhances the activity of β-lactam antibiotics against many resistant strains of bacteria. Presently, drugs containing amoxicillin and clavulanic acid have been widely used and given clinically, since it exhibits potent antibacterial activity against many resistant strains of bacteria.

Clavulanic acid represented by the above formula (I), and salts and esters thereof are disclosed in Belgium Patent No. 827,926. The process of manufacturing clavulanic acid by submerge fermentation of Streptomyces sp. microorganisms such as *Streptomyces clavuligerus, Streptomyces jumonjinensis* and *Streptomyces katsurahamanus* has been described in British Patent No. 1,508,977.

A variety of methods to recover clavulanic acid from the fermentation solution are stated in the above-mentioned British Patent. According to those methods, some standard techniques such as solvent extraction of aqueous clavulanic acid and ion exchange chromatography were employed. Nevertheless, those methods are disadvantageous in that the low-purity final product containing a small amount of toxic impurities has obtained occasionally, thus a novel method for manufacturing pharmaceutically acceptable clavulanic acid and salts thereof with non-toxicity and high purity is still required.

Meantime, another method of manufacturing potassium clavulanate from tertiary butylamine salt, an intermediate of clavulanic acid, was described in European Patent No. 0,026,044. According to the method, crude clavulanic acid was extracted with ethyl acetate, and the same volume of acetone was added as a co-solvent and then tertiary butylamine added thereto so as to crystalize the tertiary butylamine salt of clavulanic acid to isolate the salt as an intermediate. However, large amount of solvent is required in the process because large amount of acetone should be added to the ethyl acetate extract prior to the treatment with tertiary butylamine, and acetone solvates of various composition between 2% and 8% in proportion to the tertiary butylamine are formed. In addition, severe disadvantage is involved due to the use of tertiary butylamine which is highly toxic ($LD_{50}$ to rats in case of oral administration: 180 mg/kg) and volatile (b.p: 44.4° C., 760 mmHg) ["Dangerous Properties of Industrial materials", fifth ed., N. Irving Sax, and "Chemical Rubber Company Handbook of Chemistry and Physics", 53rd. ed., 1972–1973, page 400]. Therefore, the use of tertiary butylamine in an industrial scale may cause a danger to the workers of the industry.

Furthermore, since tertiary butylamine is water-soluble in all proportions, it is difficult to be recovered from the aqueous waste after the removal of the solvents. This may cause an economical disadvantages as well as possible contamination problems owing to the tertiary butylamine contained in the waste fluid of the factory. Further, in case that a large amount of solvent mixture is used as disclosed in the said patent, an additional process for recovering solvent is required so that enormous economic loss occurs.

Under these circumstances, use of other amines and alternative solvent systems have intensively been studied. For example, several amine salts of clavulanic acid have been described in the patent literature of GB-A-1508977, BE-A-862211 and GB-A-1543563. According to the said literatures, it is noted that amine salt of clavulanic acid is formed with secondary or tertiary amines, or primary amines of which the side chain contains secondary or tertiary alkyl unit. However, most of these amines are inadequate for manufacturing clavulanate salts or to be used as an intermediates for the manufacture thereof due to the formation of amine salts of clavulanic acid having hygroscopicity and/or toxicity.

Further, another process for manufacturing clavulanate salt from tertiary octyl amine salt having relatively low toxicity and volatility was described in British Patent No. 2,264,944. Nevertheless, the process also has some defects in that the process still is complicated because a process for the formation of amine salt of clavulanic acid as an intermediate step for obtaining a pharmaceutically acceptable clavulanic acid; economic or environmental problems may be caused due to the use of large amount of solvent; and recovery of the solvent is not easy.

DISCLOSURE OF INVENTION

The present inventors have, through intensive studies, succeeded in developing a simple method, free from the said defects of the prior arts, for manufacturing clavulanic acid and its pharmaceutically acceptable salts without forming amine salt of clavulanic acid.

Thus, the present invention pertains to a process for manufacturing alkali metal salts of clavulanic acid wherein clavulanate anion from the culture of mutant strain called *Streptomyces clavuligerus* NRRL 3585 is adsorbed on anion exchange resin; the anion is eluted with aqueous solution of electrolyte to purify the aqueous solution of clavulanic acid; and then the solution extracted with a mixed solvent of ketone and alkyl acetate; and, after conventional treatment, alkali metal salt of alkanoic acid dissolved in ketone or alkanol solvent is added to the extract to obtain alkali metal salt of clavulanic acid.

During the extraction process, the desirable pH of the aqueous solution is between 1 and 2 so that clavulanic acid of the aqueous phase could be transferred into the solvent layer, and the extraction is preferably performed at a temperature between 0° to 5° C. In order to get a preferable result, the aqueous solution should contain at least 10 mg/ml, preferably more than about 20 mg/ml of clavulanic acid therein.

Alkyl acetate solvent used in the extraction process may be selected from the group consisting of ethyl acetate, methyl acetate, propyl acetate and n-butyl acetate; among them, the use of ethyl acetate is more desirable. As a ketone solvent, methyl ethyl ketone or methyl isobutyl ketone may be used; but methyl isobutyl ketone is more preferable.

When a solvent mixture of ethyl acetate and methyl isobutyl ketone is used as a extraction solvent, the content of methyl isobutyl ketone is preferably 15 to 70%, more preferably 15 to 40%, and most preferably 18 to 25%. In case of methyl isobutyl ketone having less than 15% in its content, it has been proved that potassium clavulanate can not easily be crystallized. If the content of methyl isobutyl ketone exceeds 70% or it is used alone as a solvent, high boiling point of methyl isobutyl ketone may lead to a prolonged time of concentration after extraction, and high yield can not be expected.

As an alkanol solvent, n-butyl alcohol is desirably used. As an alkali metal salt of alkanoic acid, potassium 2-ethylhexanoate is preferably used.

To adjust pH during the extraction process, inorganic acid, preferably sulfuric acid may be employed.

The afore-mentioned term, "conventional treatment" of the extract means a process of drying over a drying agent such as anhydrous magnesium sulfate, filtering or concentrating the extract. It is more desirable to remove colored impurities from the extract by treating with activated carbon.

During the process of the present invention, alkali metal salt of alkanoic acid includes sodium or potassium salt thereof. Among these, potassium 2-ethyl hexanoate is particularly preferred. The moisture contained in the product thus obtained can be removed by adding acetone to the alkali metal salt formed henceforth and slurring.

The present invention shortening a step of amine formation requires less amount of solvent and provide a better yield compared to the existing methods of manufacturing clavulanic acid salt, as well as it may provide an economical and safe method by preventing possible dangers involved in handling of toxic amine compounds.

BEST MODE FOR CARRYING OUT THE INVENTION

Now, the present invention is further described by referring to the following examples. However, the present invention should not be understood to be limited to the examples.

EXAMPLE 1

100 ml of the solvent mixture of ethyl acetate and methyl isobutyl ketone (4:1) already cooled to 5° C. was added to 100 ml of aqueous solution containing clavulanic acid (12 mg/ml). While agitating the mixture, 50% sulfuric acid was slowly added in order to control pH at 1.5. After extracting the said mixture, the extracts are separated. The remaining aqueous solution was further extracted with 100 ml of the solvent mixture three times. Anhydrous magnesium sulfate (10 g) and activated carbon(10 g) were added to the combined extract, and the resultant mixture was agitated at 5° C. for 30 minutes. The mixture was suction-filtered through a filter, and the remaining material was washed with 50 ml of methyl isobutyl ketone. A solution of potassium 2-ethylhexanoate (1.5 equivalent) dissolved in methyl isobutyl ketone was slowly added to the said extract, and the mixture was agitated at 5° C. for 2 hours. The crystalline product was filtered and slurried with acetone at the same temperature for 2 hours. The crystalline was dried in a vacuum desiccator (30° C.) for about 5 hours to obtain 1.07 g of potassium clavulanate (yield: 73%).

EXAMPLE 2

The mixed-solvent extract of Example 1 was concentrated to 10% and treated with activated carbon, and then agitated at 5° C. for 20 minutes. The mixture was suction-filtered through a filter, and the remaining material was washed with methyl isobutyl ketone. A solution of potassium 2-ethylhexanoate (1.5 equivalent) dissolved in methyl isobutyl ketone was slowly added to the said extract, and the mixture was agitated at 5° C. for 2 hours. The crystalline product was filtered and slurried with acetone at the same temperature for 2 hours and was dried in a vacuum desiccator (30° C.) for about 5 hours to obtain 1.08 g of potassium clavulanate (yield:, 74%).

EXAMPLE 3

The reaction was conducted in the same manner as Example 2 except that n-butyl alcohol was used as a solvent for dissolving potassium 2-ethylhexanoate to obtain 1.04 g of potassium clavulanate (yield: 71%).

What is claimed is:

1. A process for manufacturing alkali metal salt of clavulanic acid consisting essentially of:

extracting impure clavulanic acid in aqueous solution by a solvent mixture of ketone and alkyl acetate under acidic condition, wherein the ketone content of the solvent mixture is 15 to 70%, and adding thereto a solution of alkali metal salt of alkanoic acid dissolved in ketone or alkanol solvent to obtain pure alkali metal salt of clavulanic acid.

2. The process according to claim 1, wherein the ketone solvent is selected from the group consisting of methyl ethyl ketone and methyl isobutyl ketone, the alkyl acetate is ethyl acetate, and the alkanol solvent is n-butyl alcohol.

3. The process according to claim 2, wherein the ketone content of the solvent mixture of ketone and alkyl acetate is 15 to 40%.

4. The process according to claim 1, wherein the alkali metal salt is potassium salt.

5. The process according to claim 1, wherein the alkali metal salt of alkanoic acid is potassium 2-ethylhexanoate.

6. The process according to claim 2, wherein the alkali metal salt is potassium salt.

7. The process according to claim 2, wherein the alkali metal salt of alkanoic acid is potassium 2-ethylhexanoate.

* * * * *